US010874561B1

United States Patent
Murphy et al.

(10) Patent No.: US 10,874,561 B1
(45) Date of Patent: Dec. 29, 2020

(54) CASTING TAPE PACKAGE SYSTEM

(71) Applicant: ANDOVER HEALTHCARE, INC., Salisbury, MA (US)

(72) Inventors: Thomas S. Murphy, Hillsboro Beach, FL (US); Khaled El-Tahlawy, Raleigh, NC (US); Julie K. Gatto, Chelmsford, MA (US); James T. Boyle, North Andover, MA (US)

(73) Assignee: Andover Healthcare, Inc., Salisbury, MA (US)

( * ) Notice: Subject to any disclaimer, the term of this patent is extended or adjusted under 35 U.S.C. 154(b) by 169 days.

(21) Appl. No.: 16/001,591

(22) Filed: Jun. 6, 2018

Related U.S. Application Data

(60) Provisional application No. 62/516,765, filed on Jun. 8, 2017.

(51) Int. Cl.
| | |
|---|---|
| *B65D 81/24* | (2006.01) |
| *A61F 15/00* | (2006.01) |
| *A61L 15/12* | (2006.01) |
| *B65D 81/32* | (2006.01) |

(52) U.S. Cl.
CPC ............ *A61F 15/002* (2013.01); *A61L 15/12* (2013.01); *B65D 81/3266* (2013.01)

(58) Field of Classification Search
CPC ..... B65D 81/3266; A61F 15/002; A61L 15/12
USPC ................................. 206/205, 207, 210, 494
See application file for complete search history.

(56) References Cited

U.S. PATENT DOCUMENTS

| | | | | |
|---|---|---|---|---|
| 4,537,184 A | * | 8/1985 | Williams, Jr. | ........... A61F 13/04 602/8 |
| 5,318,504 A | * | 6/1994 | Edenbaum | .............. A61L 15/08 602/6 |
| 5,620,095 A | * | 4/1997 | Delmore | ............... A61F 15/001 206/438 |
| 5,762,623 A | | 6/1998 | Murphy et al. | |
| 5,984,088 A | * | 11/1999 | Dietz | .................... A61F 15/001 206/205 |
| 5,988,371 A | * | 11/1999 | Paley | ..................... A47K 10/32 206/229 |
| 6,156,424 A | | 12/2000 | Taylor | |
| 7,172,565 B2 | * | 2/2007 | Termanini | ........... A61F 5/05825 602/8 |
| 8,779,230 B2 | | 7/2014 | El Tahlawy et al. | |
| 2003/0060798 A1 | * | 3/2003 | Fischer | ................ A61N 1/0448 604/501 |
| 2005/0158539 A1 | | 7/2005 | Murphy et al. | |
| 2006/0009721 A1 | * | 1/2006 | Evans | ..................... A61F 5/058 602/5 |
| 2006/0073328 A1 | | 4/2006 | Murphy et al. | |
| 2006/0154546 A1 | | 7/2006 | Murphy et al. | |
| 2007/0259163 A1 | | 11/2007 | Connolly et al. | |
| 2007/0299383 A1 | | 12/2007 | Murphy et al. | |
| 2008/0014386 A1 | | 1/2008 | Murphy et al. | |
| 2008/0014387 A1 | | 1/2008 | Murphy et al. | |

(Continued)

*Primary Examiner* — Luan K Bui
(74) *Attorney, Agent, or Firm* — Brenda D. Wentz

(57) ABSTRACT

A casting tape package system is provided comprising an outer package defining a first interior portion enclosing a casting tape substrate including curable casting formulation and a second interior portion enclosing a curing agent. In certain embodiments, the curing agent is separated from the casting tape substrate by a barrier which is breakable to release the curing agent to activate the curable casting formulation.

17 Claims, 9 Drawing Sheets

(56) References Cited

U.S. PATENT DOCUMENTS

| | | |
|---|---|---|
| 2008/0031931 A1 | 2/2008 | Gunn |
| 2009/0075042 A1 | 3/2009 | Murphy |
| 2009/0216163 A1* | 8/2009 | Evans ................... A61F 13/10 |
| | | 602/6 |
| 2010/0055157 A1 | 3/2010 | Gunn |
| 2012/0238933 A1 | 9/2012 | Murphy et al. |
| 2013/0204171 A1* | 8/2013 | Spector .............. A61F 5/05825 |
| | | 602/8 |
| 2014/0276322 A1 | 9/2014 | Murphy et al. |
| 2015/0297861 A1* | 10/2015 | Passalaqua ......... A61M 25/002 |
| | | 206/210 |
| 2016/0166440 A1 | 6/2016 | El-Tahlawy et al. |
| 2017/0203541 A1 | 7/2017 | El-Tahlawy et al. |
| 2017/0321062 A1 | 11/2017 | Murphy et al. |

* cited by examiner

CASTING TAPE PACKAGE SYSTEM

CROSS-REFERENCE TO RELATED APPLICATION

This application claims the benefit of provisional application No. 62/516,765 filed Jun. 8, 2017. The aforementioned application is incorporated herein by reference in its entirety.

BACKGROUND

The present invention relates to pre-impregnated casting material packaged alongside an activating or curing material for orthopedic casting.

Existing orthopedic casting tapes require multiple steps prior to application. Current casting tapes comprise a roll of casting tape substrate that has been pre-impregnated with a curable pre-polymer resin. Commonly, casting tape that has been pre-impregnated with water curable resin is packaged for storage until use. In order to activate the curable pre-polymer resin and form a rigid cast, the casting tape must be removed from its packaging and immersed in a separate container of water, e.g., tap water, which initiates curing of the pre-polymer resin. Once the resin has been activated, the tape may then be wrapped or otherwise molded around the desired area or limb before it eventually becomes rigid.

The present disclosure contemplates a new casting tape packaging system that allows the user to initiate the curing process in the original storage packaging, without the need for a separate container of water or a separate dipping step. This can save medical personnel time in the preparation and application process and storage space and, moreover, reduce the amount of necessary equipment. Such system can also eliminate the need for a separate water source and provide for greater mobility of use.

SUMMARY

In one aspect, the present disclosure provides a casting tape system for providing a means of packaging a casting substrate, a casting formulation, and a curing agent in one packaging system.

Certain embodiments of the present disclosure provide a casting tape packaging system comprising an outer packaging, the outer packaging enclosing a casting tape substrate that has been pre-impregnated or pre-coated with a curable casting formulation. The casting tape substrate is separated from an activating agent within the outer packaging by way of a barrier. The activating agent may be released onto the casting tape substrate by application of force onto the barrier. Once released, the outer packaging may be agitated or massaged to aid in mixing the activating agent with the casting formulation in the casting tape substrate. The activated casting material may then be applied to a patient.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
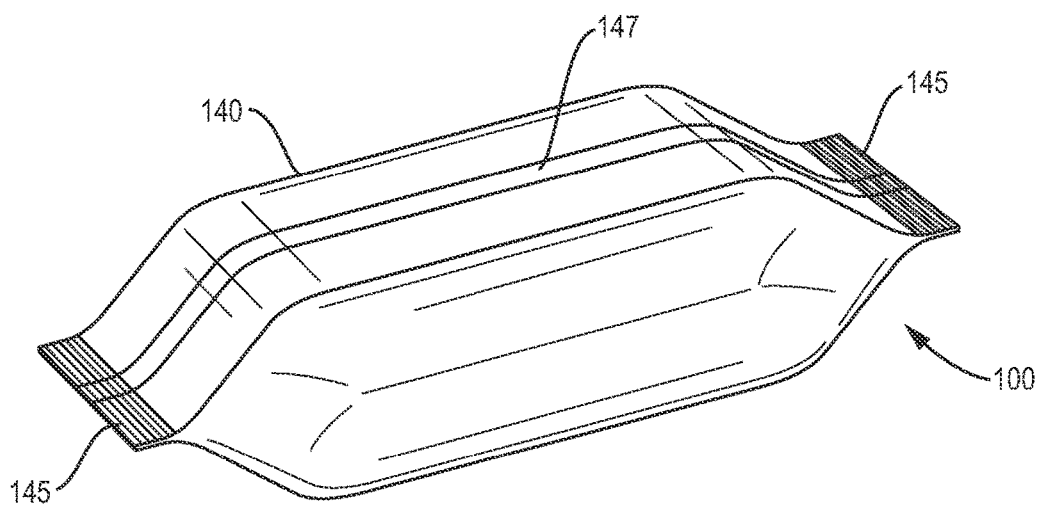
FIG. 1 is a perspective view of a casting tape package system.
Figure 2:
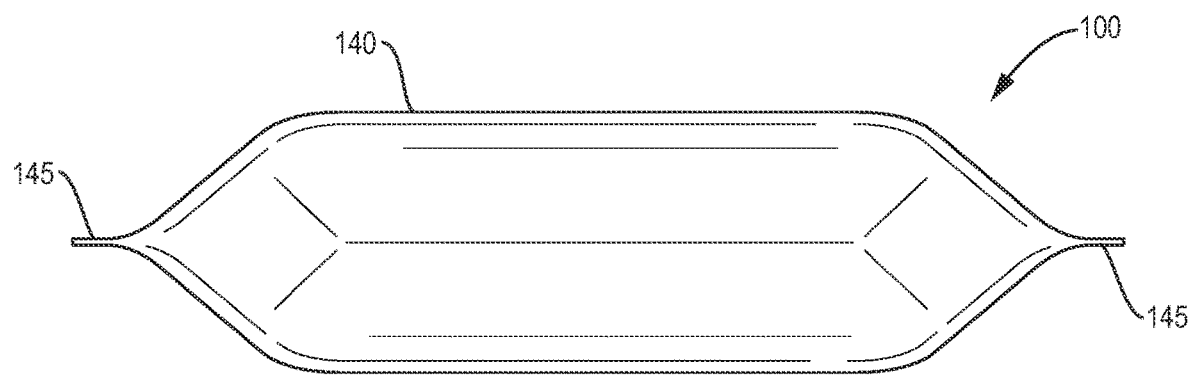
FIG. 2 is a side view of the casting tape package system of FIG. 1.

Referring now to the drawings, wherein like reference numerals represent like or analogous components throughout the several views, FIGS. 1-2 illustrate a casting tape package system, generally designated 100. The package system 100 includes an outer container, such as a bag or pouch 140. In certain embodiments, the outer bag 140 is formed of a polymer film, such as a heat sealable polymer film. In certain embodiments, the outer pouch 140 is formed of a polymer film and includes one or more sealed seams, such as sealed transverse ends 145 and a sealed longitudinal seam 147. The seams 145, 147 may be sealed via heat sealing, radio frequency (RF) sealing, adhesive sealing, and the like. The package system may include a tearing notch indicating a line of preferential tearing for ease of opening of the package.

The bag 140 includes at least one interior compartment for receiving a roll of casting tape 110 and at least one interior compartment for receiving a curing agent 130. In certain embodiments, the curing agent is a liquid. In certain embodiments, the curing agent is water. In certain embodiments, other curing agent materials are contemplated including non-liquid materials, including solid and gaseous materials. The package system in accordance with this disclosure will be described herein primarily by way of reference to the preferred embodiments wherein the casting tape 110 is pre-impregnated with a water-curable pre-polymer resin and the curing agent 130 is water. However, it will be recognized that the present development could be adapted for use with alternative resin/curing agent systems, including systems where the curing agent is a materials selected from one or more solids, liquids, gasses, gels, powders, particulates, suspensions, emulsions, and any combination thereof, as would be understood by persons skilled in the art. In preferred embodiments, the formulation of the pre-polymer resin and/or the quantity of curing agent are selected to allow the casting tape to remain pliable for a predetermined period of time after the casting tape is mixed with the curing agent 130. The casting material 110 and activating material 130 are separated until use.

Again, in certain embodiments, the activating material 130 is water, although it is recognized that the material 130 may comprise other substances to react with, activate, and/or cure the curable pre-polymer resin.

In certain embodiments, the casting material 110 is made of a fabric, e.g., a woven fabric, such as a polyester fabric or fiberglass fabric. In certain preferred embodiments, the fabric has an open structure. The fabric is impregnated with the curable pre-polymer resin. In certain embodiments, the fabric is coated or impregnated with a pre-polymer, such as polyurethane pre-polymer. It is contemplated that any curable resin suitable for casting may be used for the curable pre-polymer resin.

In the illustrated embodiments, when the casting tape is intended to be used, an internal barrier, generally designated as barrier 120, is broken, allowing the curing agent 130 to mix with the casting tape 110. The package 100 may be shaken, agitated, massaged, and/or kneaded to aid in mixing the activating material 130 with the curable pre-polymer resin that is impregnated with the casting material 110. In certain embodiments, the use of an open structure (e.g. open weave) fabric allows for faster and better absorption of the activating agent 130. The activated casting material may then be applied to a patient, for example, to set a broken bone. In certain embodiments, the curable pre-polymer resin is formulated such that it will remain pliable or supple for a period of time after activation and harden soon after application.

In certain embodiments, the barrier 120 is formed of a material that is weaker than the outer packaging 140 such that the barrier may be preferentially broken upon application of force to release the activating material 130 for mixing with the casting material 110 prior to opening the outer packaging 140.

In certain embodiments, the casting material 110 is wound up into a roll. In certain alternative embodiments, the casting material 110 is cut into one or more discrete strips of desired length or into other shapes, which may be packaged together or individually.

In certain embodiments, the casting material 110 is 3 inches wide and may be of any desired length, e.g., 4 yards long. In certain embodiments, the casting material 110 is 4 inches wide and of any desired length, e.g., 4 yards long. Other widths and lengths are also contemplated.

In certain embodiments, two or more rolls of casting material 110 may be included in one package.

Figure 3:
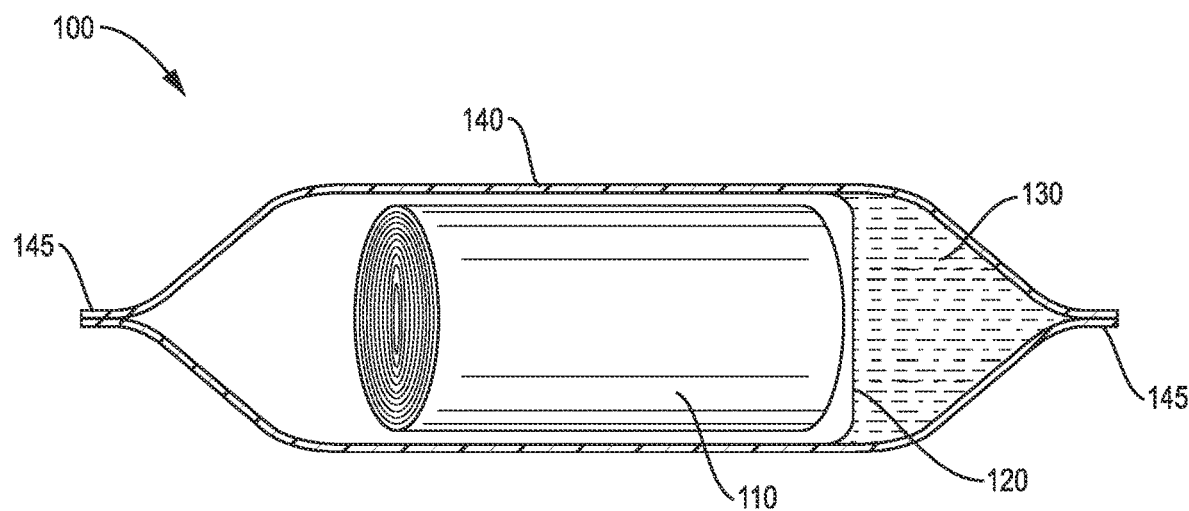
FIG. 3 is a side cross-sectional view of the casting tape package system according to an exemplary embodiment, illustrating a barrier separating an activating agent from a roll of casting material.
Figure 4:
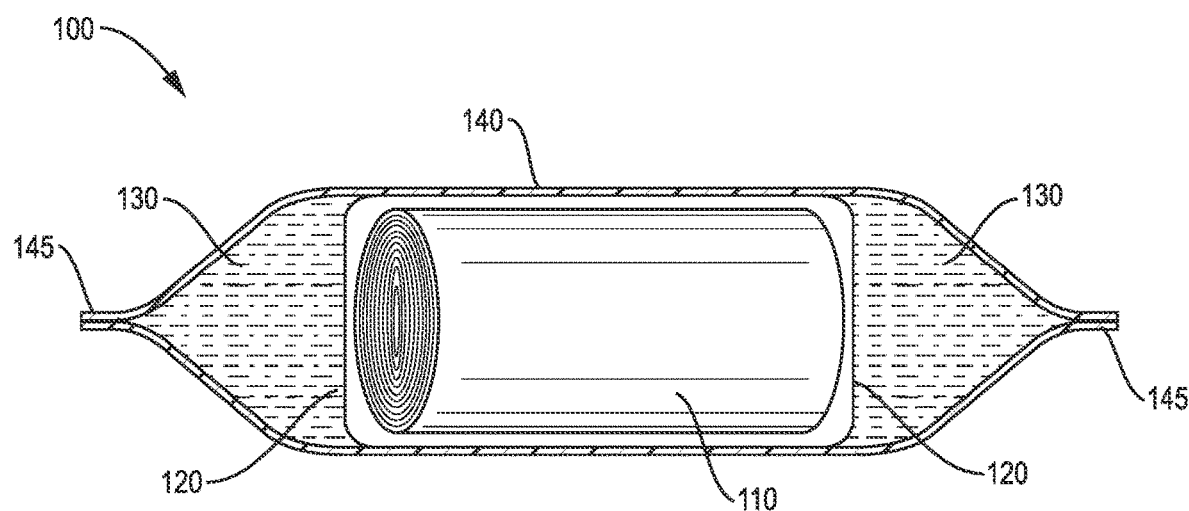
FIG. 4 is a side cross-sectional view of a casting tape package system according to an exemplary embodiment, illustrating two barriers, each separating activating agent from a roll of casting material.
Figure 5:
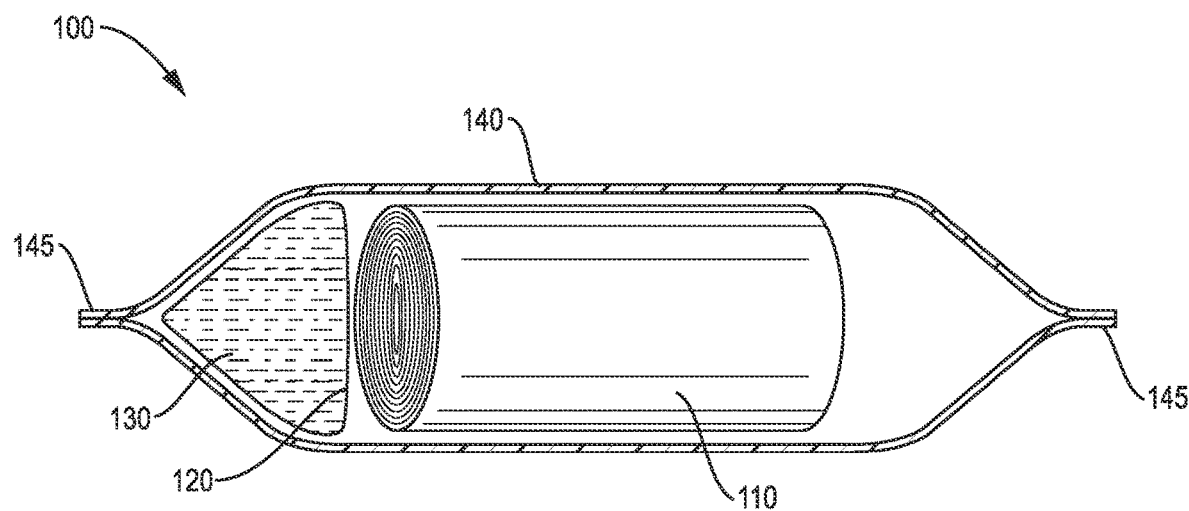
FIG. 5 is a side cross-sectional view of a casting tape package system according to an exemplary embodiment, illustrating a pouch detached from the outer packaging and containing activating agent.
Figure 6:
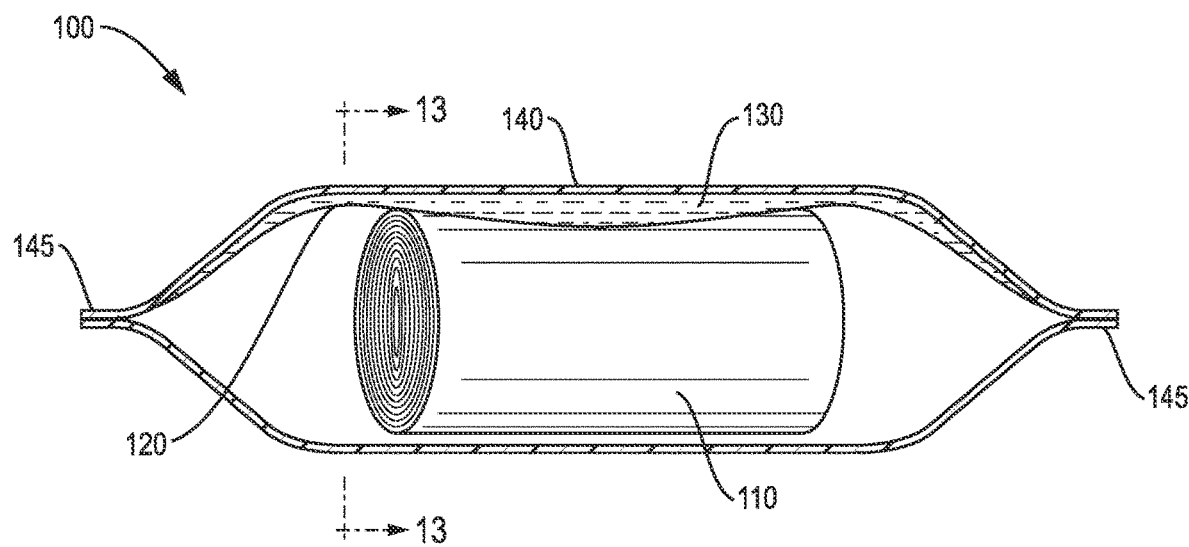
FIG. 6 is a side cross-sectional view of a casting tape package system according to an exemplary embodiment, illustrating a barrier extending substantially across a side wall or panel of the package across the (across the top panel of the package in the orientation shown) and separating an activating agent from a roll of casting material.
Figure 7:
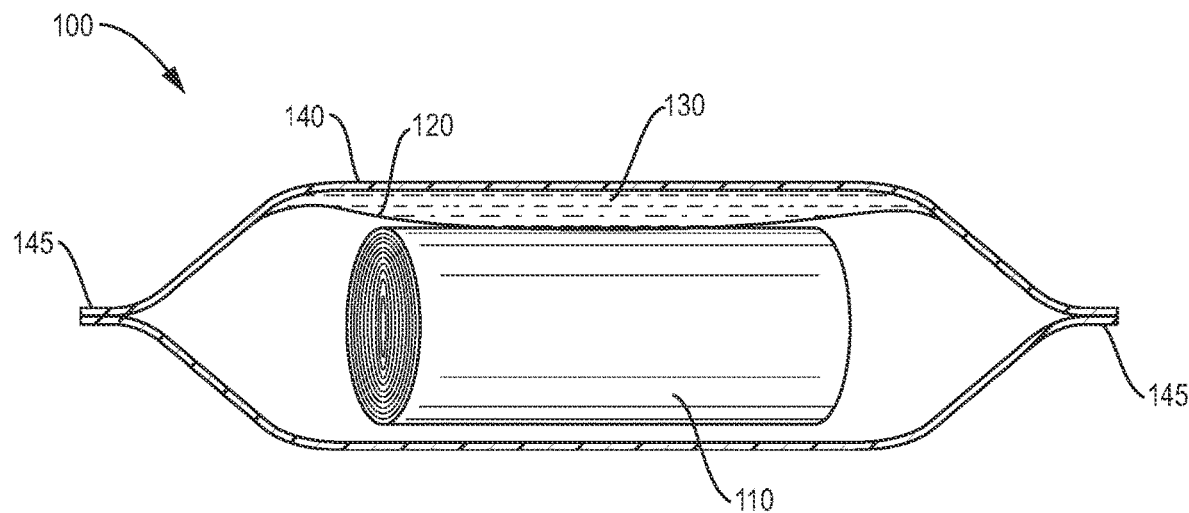
FIG. 7 is a side cross-sectional view of a casting tape package system according to an exemplary embodiment, illustrating a blister-type barrier separating an activating agent from a roll of casting material.
Figure 8:
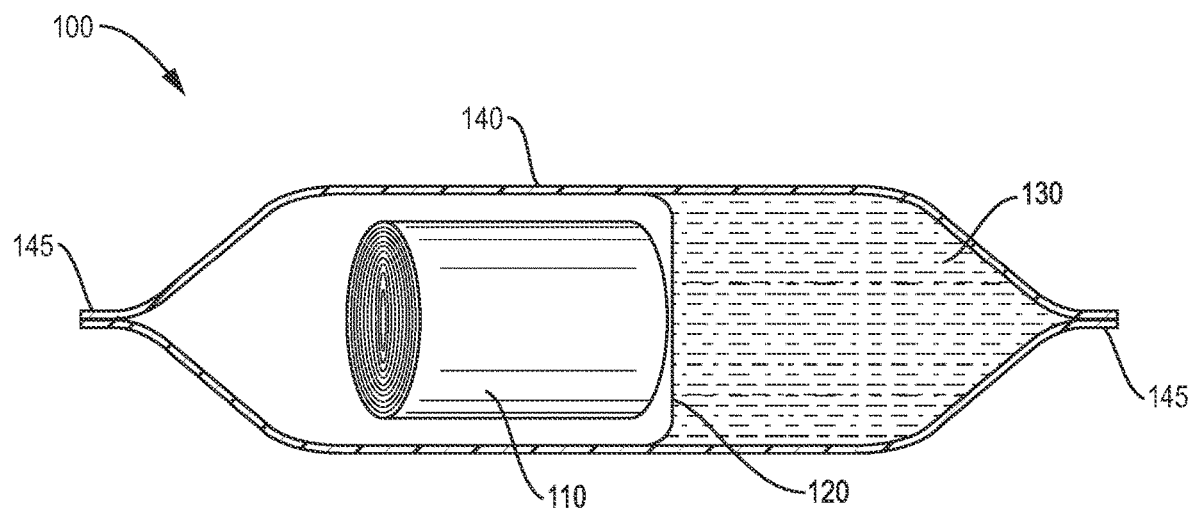
FIG. 8 is a side cross-sectional view of a casting tape package system according to an exemplary embodiment, illustrating a barrier separating an activating agent from a roll of casting material.
Figure 9:
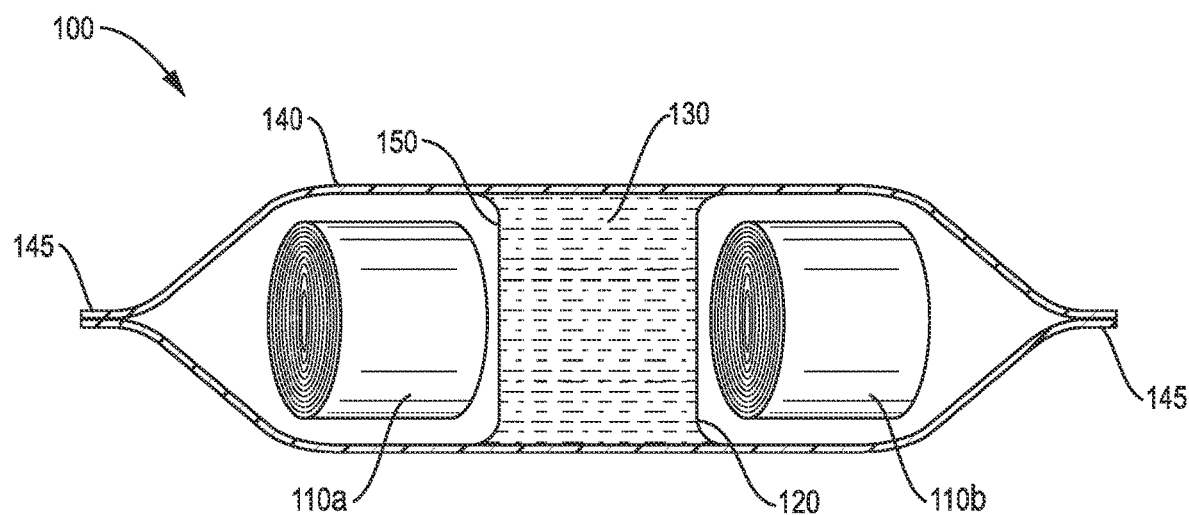
FIG. 9 is a cross-sectional side view of a casting tape package system according to an exemplary embodiment, illustrating two barriers separating two rolls of casting material from the activating agent contained within a central compartment.
Figure 10:
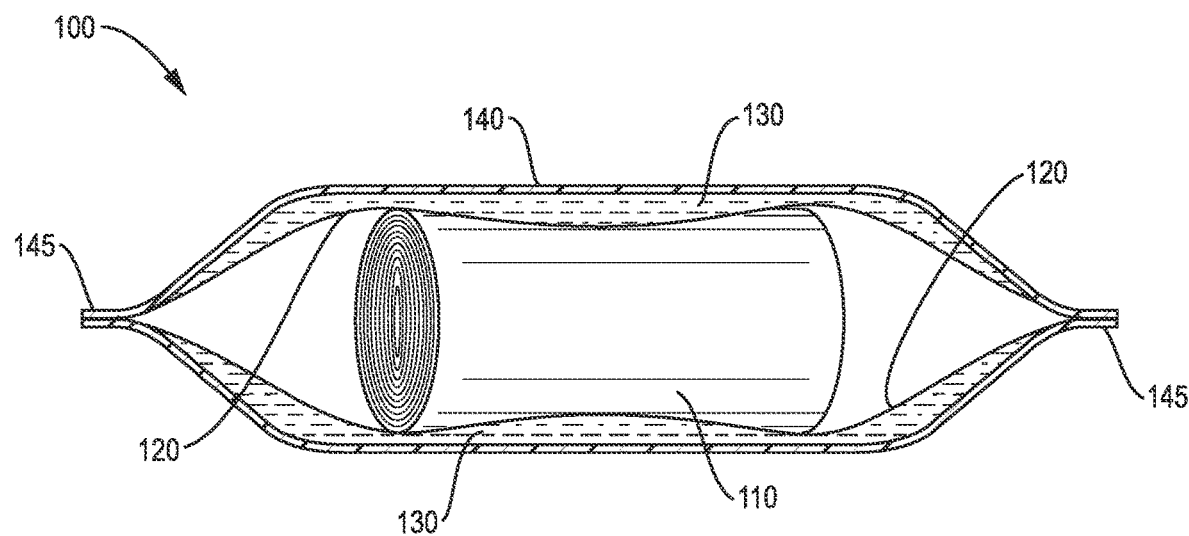
FIG. 10 is a cross-sectional side view of a casting tape package system according to an exemplary embodiment, illustrating two barriers along outer packaging sidewalls separating respective pockets of activating agent from a roll of casting material.
Figure 11:
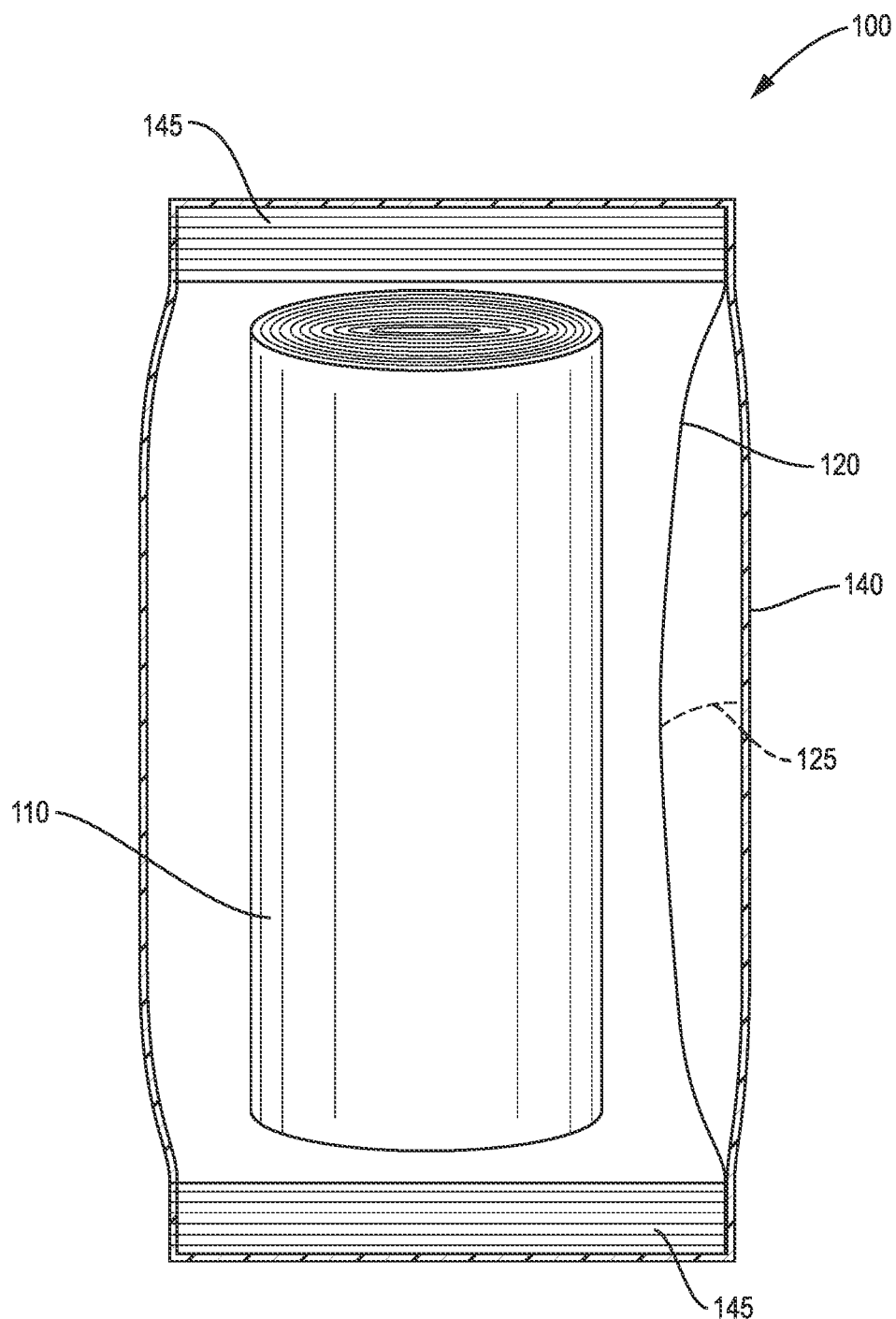
FIG. 11 is a cross-sectional view of a casting tape package system according to an exemplary embodiment, illustrating a barrier separating activating agent from a roll of casting material, wherein the barrier includes a line of preferentially breaking material.
Figure 12:
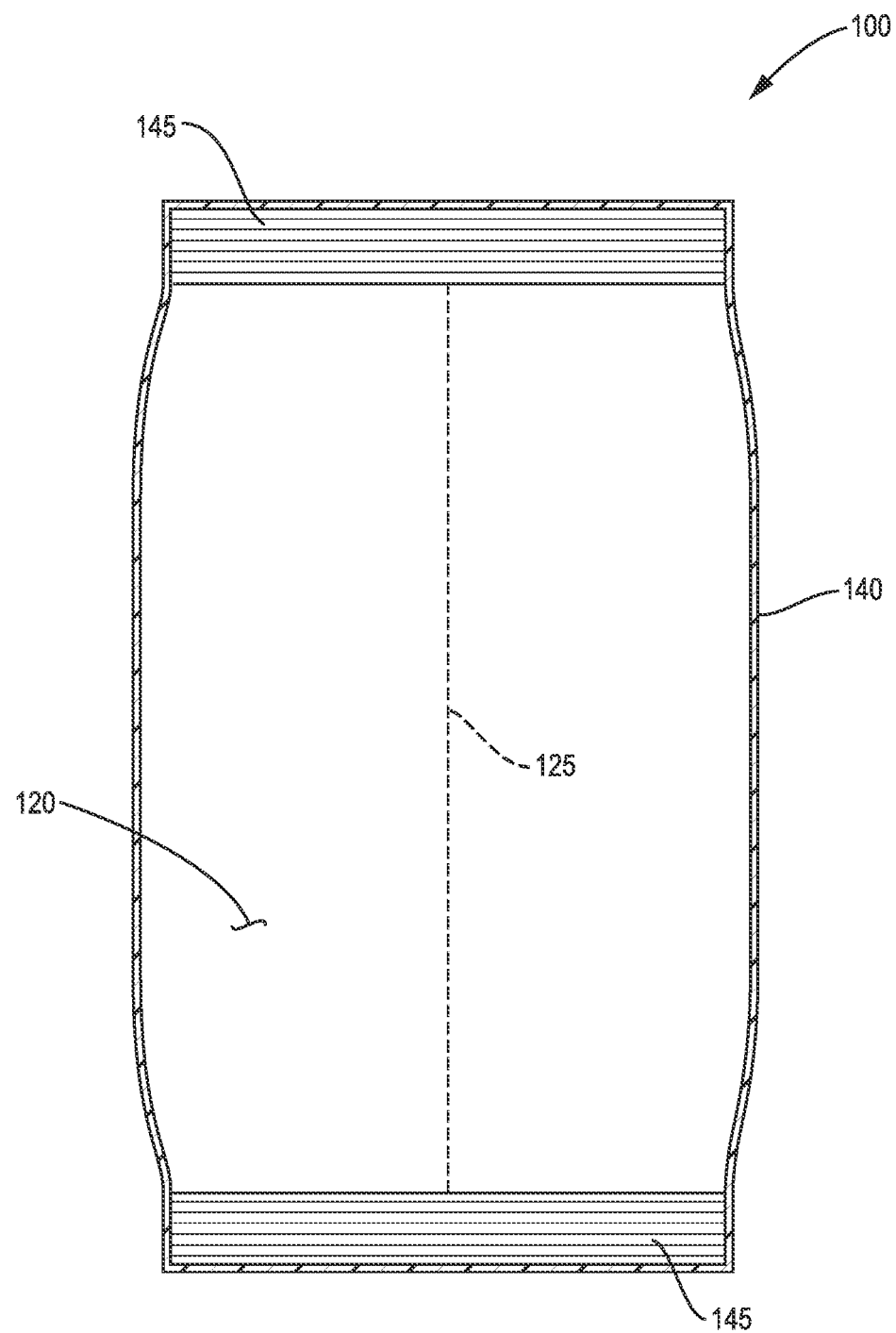
FIG. 12 is a side view of a casting tape package system according to the exemplary embodiment illustrated in FIG. 6, with the outer side panel cut away, illustrating the inner surface of a barrier that is sealed to the inner surface of the outer packaging, and wherein the barrier includes a line of preferential breaking.
Figure 13:
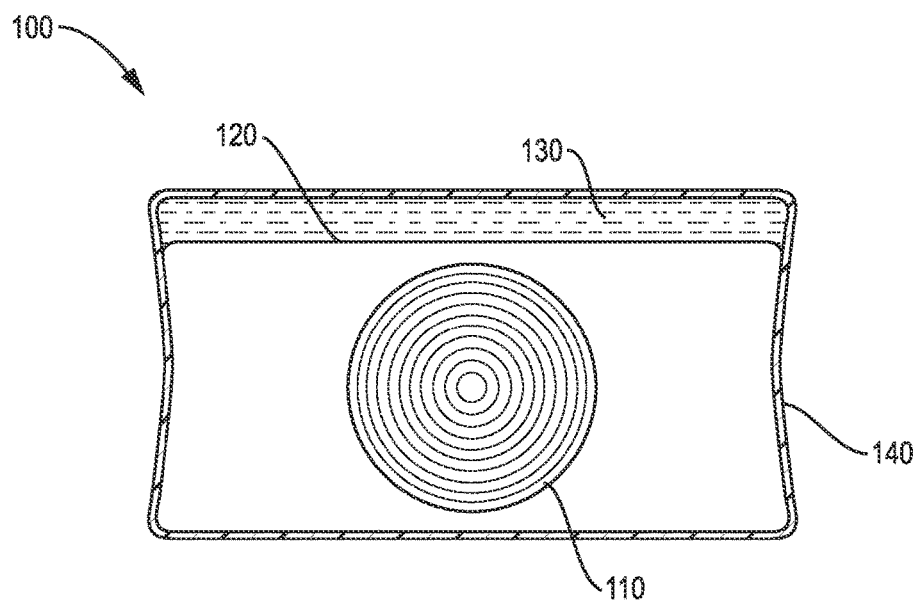
FIG. 13 is an end cross sectional view of a casting tape package system according to the exemplary embodiment illustrated in FIG. 6.

FIGS. 3-11 illustrate exemplary embodiments of the casting tape package system 100. In certain embodiments, at least one breakable or frangible barrier 120 is attached to the inner surface of the outer packaging 140, effectively dividing the package into at least two compartments and separating the casting material 110 from the material 130. The barrier 120 is sealed to the inner surface of the outer packaging 140, such that the activating material is unable to pass through the sealed edges or seams. In FIGS. 3 and 8, the barrier is sealed to the top, bottom, and side panels of the inner surface of the packaging 140, such that the material is contained in one end of the package system 100. In FIG. 4, two such barrier walls 120 define compartments containing the activating agent 130, e.g., activating liquid, at substantially opposite ends of the packaging structure. In FIG. 6, the barrier 120 is sealed to an inner surface of a side panel of the outer packaging 140, and extends between the sealed seams 145 disposed at substantially opposite ends of the package. In FIG. 7, the barrier 120 is sealed to an inner surface of a side panel of the outer packaging 140, and is sealed along a side panel at an intermediate position between the ends of the package. FIG. 10 illustrates an embodiment similar to FIG. 6 or 7, but wherein there are two barriers 120 sealed along the inner surfaces of opposing side panels of the packaging 140 forming two compartments, each containing activating agent 130. FIG. 11 illustrates an embodiment similar to FIG. 3, but wherein there is one barrier 120 forming one compartment containing activating agent 130 sealed to the inner surface of the top panel of the packaging 140.

Figure 14:
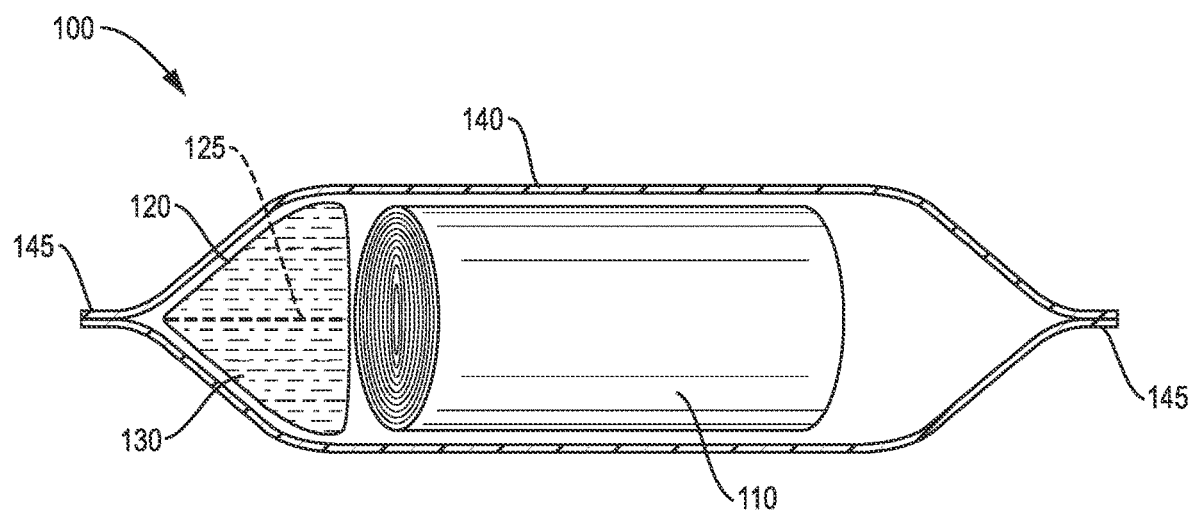
FIG. 14 is a side cross-sectional view of a casting tape package system according to an exemplary embodiment, illustrating a pouch containing an activating agent within and detached from the outer packaging, the pouch having a line of weakened material.

In certain embodiments, at least one barrier 120 defines at least one self-contained or separately formed sealed pouch, bag, sachet, packet, or the like, containing material 130 which is contained within, but otherwise not attached to, the outer packaging 140, such as is illustrated in FIGS. 5 and 14-16. In FIGS. 5 and 14, the packaging system includes one separately formed packet 120 containing activating agent 130 is disposed adjacent the roll of casting material 110 at a first end of the outer packaging 140. In certain embodiments, the pouch has a shape or profile which is generally configured to fit within the shape or profile of at least an inner portion of the outer packaging 140 such that the shape maximizes the volume of the pouch that is able to fit between the outer packaging 140 and casting material 110.

Figure 15:
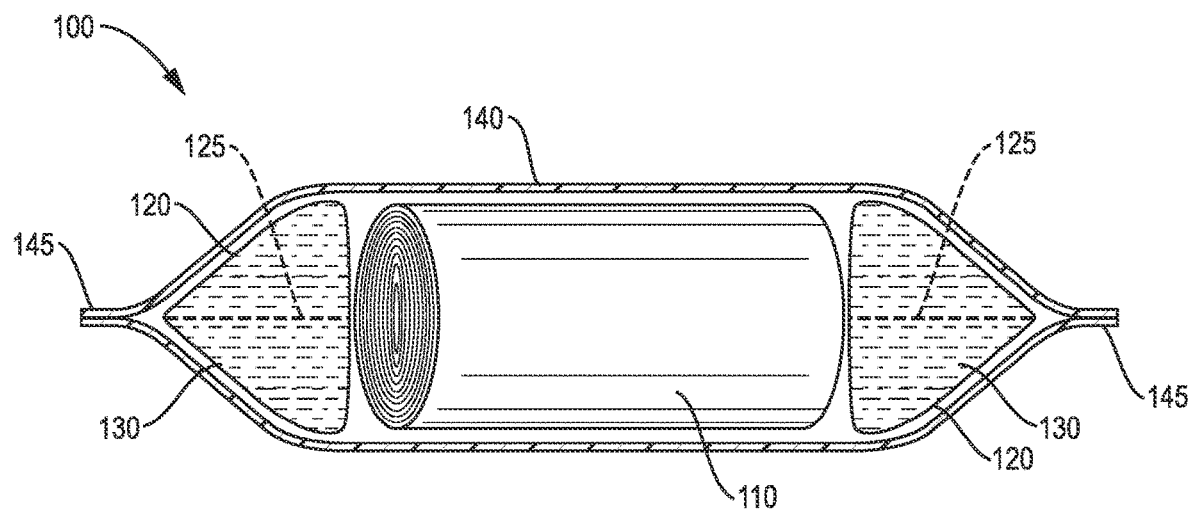
FIG. 15 is a side cross-sectional view of a casting tape package system according to an exemplary embodiment, illustrating two pouches detached within and detached from the outer packaging with a line of weakened material on each pouch.

In FIG. 15, a packaging system similar to the embodiment shown in FIG. 14 is shown, but wherein there are two separately formed packets 120 containing the material 130, e.g., activating liquid, which are disposed at substantially opposite ends of the roll of casting material 110 within the outer packaging 140. In certain embodiments, the pouches have a shape or profile which generally matches the shape or profile of the ends of the outer packaging 140. By providing multiple liquid compartments on opposite sides of the roll, distribution of the liquid is enhanced and/or the user can open a desired number of compartments to control the degree of wetting of the casting tape material. In certain embodiments (not illustrated), the multiple compartments or pouches for activating material 130 may be situated anywhere in the packaging system 100 convenient for packaging purposes and/or for ideal distribution of material 130.

Figure 16:
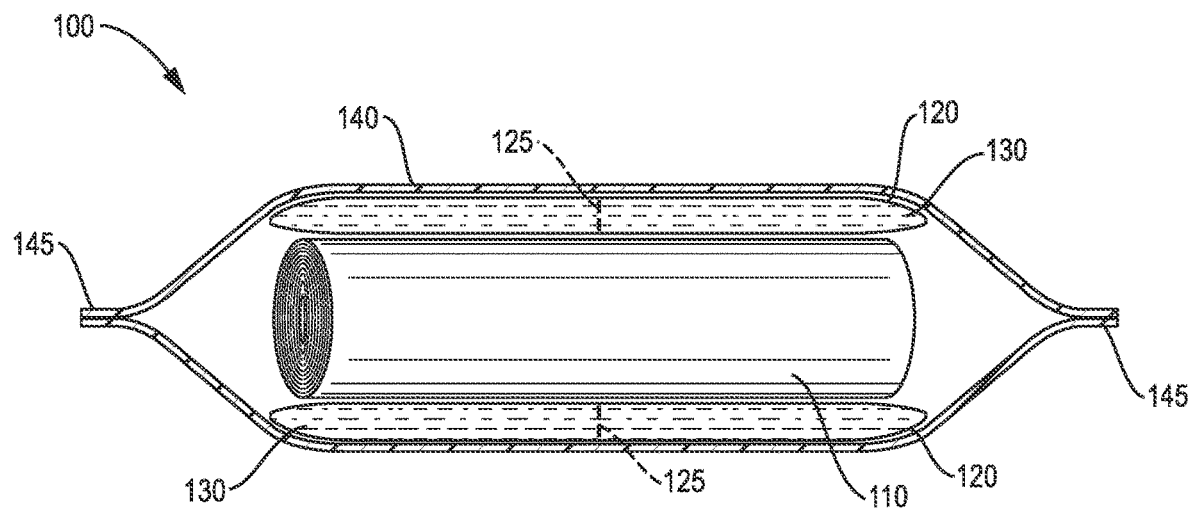
FIG. 16 is a side cross-sectional view of a casting tape package system according to an exemplary embodiment, illustrating two pouches within and detached from the outer packaging with a line of weakened material on each pouch.

In FIG. 16, a packaging system similar to the embodiment shown in FIG. 15 is shown, but wherein there are two separately formed packets 120 containing the liquid 130, which are each disposed between the roll of casting material 110 and a sidewall of the outer packaging 140. In alternative embodiments, the two pouches appearing in FIG. 16 may be replaced with a single separately formed pouch disposed between the roll 110 and a sidewall of the outer packaging 140.

The barrier 120 is made of a material that prevents the activating agent 130 from passing through from one compartment to another prior to use. The barrier 120 may be sealed via heat sealing, RF sealing, adhesive sealing, and the like.

The barrier 120 is formed of a material which will break or rupture upon application of a force or pressure that is less than the force or pressure required to break or rupture the outer packaging material 140. In certain illustrated embodiments, the barrier 120 further comprises at least one region or line of preferential breaking 125, such as is shown in FIGS. 11, 12, and 14-16, that is more easily torn or broken when the barrier is squeezed or otherwise applied with pressure. In certain further embodiments, the weakened or frangible line is produced by scoring (e.g., mechanical scoring or laser scoring) in desired areas. Where the pouch containing activating material 130 is not sealed or attached to a panel, the area of preferential breaking is located at least on the side of the pouch facing the casting material 110, for ease of distribution of the activating material 130. In certain embodiments, the material-containing pouch has a weakened or frangible line running substantially along the barrier 120 circumference of the pouch. In certain embodiments, the barrier 120 is formed of a polymer film material having a tensile strength lower than the tensile strength of the outer packaging film 140 as well as of the sealing strength of the sealed seams 145, 147 to allow the barrier 120 material to be ruptured without rupturing the material forming the outer packaging 140 or a sealed seam of the packaging systems, e.g., seams 145 or 147. In certain embodiments wherein the barrier 120 is formed of a polymer film material having a lower tensile strength lower than the outer packaging film 140 and the sealing strength of the sealed seams 145, 147, the weakened regions 125 are optional and may be omitted.

It is recognized that a package system 100 may contain more than one barrier 120. In certain situations, it may be preferable to apply an initial layer of casting tape that has not been activated or cured. FIG. 9 shows an exemplary embodiment wherein the casting tape package system is effectively divided by two sealed barriers 120, 150 into three compartments, wherein barrier 120 is preferentially breakable with respect to the barrier 150. The package system of FIG. 9 includes two rolls of casting tape 110a, 110b in separate compartments, with a center compartment in between containing activating material 130. The user may remove the first roll of casting tape 110a for use without releasing or mixing with the activating liquid 130. The barrier 120 may then be broken to release the activating liquid 130 to activate the second roll of casting tape 110b. The activated casting tape may then be applied over the initial layer of casting tape. The activating liquid 130 from the activated casting tape will seep through to the initial layer of casting tape that was not activated, thereby activating the initial layer. This allows the initial layer to be used and/or kept in its inactive state until it is desirable to activate it. It is recognized that this method may be reversed such that the activated casting tape may be applied first and a second layer of non-activated casting tape may be applied over the activated casting tape. The activated liquid 130 from the activated casting tape will seep through the second layer that was not activated, thereby activating the second layer. In alternative embodiments, a casting tape package system 100 containing more than one roll of casting tape may include more than one barrier 120, wherein more than one barrier is breakable to activate more than one roll of casting tape at the same time. Although the barriers 120, 150 are attached to the outer packaging 140 it will be recognized that the barriers 120, 150 could be replaced with a detached, separately formed pouch containing the liquid 130 within the outer packaging 140, e.g., intermediate the rolls 110a, 110b. It is also recognized that a package system containing more than one roll of casting tape 110 may be packaged such that one compartment contains more than one roll of casting tape.

In certain embodiments, there may be more than one barrier 120 separating activating material from the casting material 110 particularly where additional material 130 is desired to be included for activating a larger amount of casting material. FIGS. 4 and 10 show exemplary embodiments wherein the casting tape package system is effectively divided by two sealed barriers 120 into three compartments, wherein both barriers 120 are breakable, each sealed barrier 120 separating activating material 130 from a center compartment containing a roll of casting tape 110.

It is recognized that a package may contain at least one barrier 120 that comprises a line of weakened material, e.g., a score line, and another barrier 120 that is formed of a lower tensile strength material. It is also recognized that a package system 100 may contain at least one barrier 120 that is sealed to the inner surface of the outer packaging and at least one barrier 120 that forms a sealed pouch that is not attached to the outer packaging (not illustrated). It is recognized that a package may contain first and second barriers wherein the first barrier has a tensile strength that is lower than a tensile strength of the outer packaging. In certain embodiments, the first barrier has a tensile strength of that is lower than a tensile strength of the second barrier.

The invention has been described with reference to the preferred embodiment. Modifications and alterations will occur to others upon a reading and understanding of the preceding detailed description. It is intended that the invention be construed as including all such modifications and alterations insofar as they come within the scope of the appended claims and their equivalents.

What is claimed is:

1. A casting tape package system comprising:
   an outer packaging, said outer packaging including a first interior portion and a second interior portion;
   a casting substrate, wherein said casting substrate is a fabric and is located in the first interior portion and includes a curable casting formulation;
   a curing agent, said curing agent located in the second interior portion; and
   a barrier disposed within the outer packaging and separating the first interior portion from the second interior portion, the barrier breakable to allow the curing agent to admix with the casting substrate, and wherein the outer packaging defines an enclosure having an inner surface, wherein the barrier is sealed to the inner surface.

2. The casting tape package system of claim 1, wherein the outer packaging is formed of a polymer film.

3. The casting tape package system of claim 1, wherein the curable casting formulation is a curable resin.

4. The casting tape package system of claim 3, wherein the curable resin is a water curable pre-polymer resin and the curing agent is water.

5. The casting tape package system of claim 3, wherein the curable resin is a polyurethane pre-polymer.

6. The casting tape package system of claim 1, wherein the fabric is selected from the group consisting of a polyester fabric, a fiberglass fabric, and an open-weave fabric.

7. The casting tape package system of claim 1, wherein the barrier is configured to form a sealed bladder.

8. The casting tape package system of claim 7, wherein the outer packaging and the bladder are separately formed and the bladder is received within an interior compartment defined by the outer packaging.

9. The casting tape package system of claim 1, wherein the barrier is formed of a material having one or both of:
   a line of preferential breaking; and
   a tensile strength which is lower than a tensile strength of the outer packaging.

10. The casting tape package system of claim 1, wherein the barrier is formed of a polymer film.

11. The casting tape package system of claim 1, wherein the casting substrate is impregnated with the curable casting formulation.

12. A casting tape package system comprising:
   an outer packaging, said outer packaging including a first interior portion, a second interior portion, and a third interior portion;
   a first casting substrate, wherein said first casting substrate is located in the first interior portion and wherein said first casting substrate includes a curable casting formulation;
   a curing agent, said curing agent located in the second interior portion;
   and a second casting substrate, wherein said second casting substrate is located in the third interior portion and also includes the curable casting formulation.

13. The casting tape package system of claim 12, further comprising a first barrier separating the first interior portion from the second interior portion, and a second barrier separating the second interior portion from the third interior portion.

14. The casting tape package system of claim 13, wherein a tensile strength of the first barrier is lower than a tensile strength of the outer packaging.

15. The casting tape package system of claim 14, wherein the tensile strength of the first barrier is lower than a tensile strength of the second barrier.

16. The casting tape package system of claim 13, wherein the outer packaging includes an inner surface and an outer surface and wherein one or both of the first barrier and the second barrier is sealed to the inner surface.

17. The casting tape package system of claim 13, wherein one or both of the first barrier and the second barrier is configured to form a bladder.

\* \* \* \* \*